US011452641B2

(12) United States Patent
Quintero et al.

(10) Patent No.: US 11,452,641 B2
(45) Date of Patent: Sep. 27, 2022

(54) WOUND CLOSURE SYSTEMS FOR REDUCING SURGICAL SITE INFECTIONS COMPRISING INCISION DRAPES FILLED WITH RELEASABLE ANTIMICROBIAL AGENTS (71) Applicant: Ethicon, Inc., Somerville, NJ (US)

(72) Inventors: Julian Quintero, Flemington, NJ (US); Robert J. Tannhauser, Bridgewater, NJ (US); Leo B. Kriksunov, Ithaca, NY (US)

(73) Assignee: Ethicon, Inc., Raritan, NJ (US)

( * ) Notice: Subject to any disclaimer, the term of this patent is extended or adjusted under 35 U.S.C. 154(b) by 532 days.

(21) Appl. No.: 16/456,727

(22) Filed: Jun. 28, 2019

(65) Prior Publication Data
US 2020/0405544 A1 Dec. 31, 2020

(51) Int. Cl.
A61F 13/00 (2006.01)
A61B 46/13 (2016.01)
A61F 13/02 (2006.01)
A61L 15/44 (2006.01)
A61L 15/58 (2006.01)
A61M 1/00 (2006.01)

(52) U.S. Cl.
CPC ........ A61F 13/00068 (2013.01); A61B 46/13 (2016.02); A61F 13/0216 (2013.01); A61L 15/44 (2013.01); A61F 13/025 (2013.01); A61L 15/58 (2013.01); A61L 2300/404 (2013.01); A61M 1/90 (2021.05)

(58) Field of Classification Search
CPC .............. A61F 13/0068; A61F 13/0216; A61F 13/025; A61B 46/13; A61B 17/08; A61B 17/085; A61L 15/44; A61L 15/58; A61L 2300/62; A61L 2300/404; A61L 26/00; A61L 26/0066; A61L 26/0038; A61L 26/02; A61L 26/0095; A61L 24/04; A61L 24/00; A61L 24/046; A61L 24/001; A61M 1/90; A61M 35/006; A61M 35/00; A61K 8/0208; A61K 9/70
USPC .............. 128/849; 424/433, 447, 445; 604/3
See application file for complete search history.

(56) References Cited

U.S. PATENT DOCUMENTS

| | | |
|---|---|---|
| 3,490,454 A | 1/1970 | Alvin |
| 3,598,123 A | 8/1971 | Zaffaroni |
| 3,691,271 A | 9/1972 | Charle |
| 4,597,960 A | 7/1986 | Cohen |

(Continued)

FOREIGN PATENT DOCUMENTS

| | | |
|---|---|---|
| WO | WO2012091457 A3 | 10/2012 |
| WO | WO2017151226 A1 | 9/2017 |

OTHER PUBLICATIONS

International Search Report dated Sep. 17, 2020 for Application No. PCT/IB2020/055501.

Primary Examiner — Erin Deery
Assistant Examiner — Daniel A Miller (57) ABSTRACT A surgical incision drape, comprises a flexible substantially flat areal substrate having an upper side and an opposing tissue-facing side, having a longitudinal axis and a pressure sensitive adhesive disposed on the tissue-facing side; at least one hollow microtubular compartment containing a flowable medical agent, said hollow microtubular compartment positioned to intersect the longitudinal axis and embedded into the substrate or positioned on the substrate.

16 Claims, 10 Drawing Sheets (56) References Cited

U.S. PATENT DOCUMENTS

| | | | |
|---|---|---|---|
| 4,643,181 A | 2/1987 | Brown | |
| 4,654,256 A | 3/1987 | Doree | |
| 5,717,005 A | 2/1998 | Richardson | |
| 6,139,856 A | 10/2000 | Kaminska | |
| 7,015,156 B2 | 3/2006 | Maldonado | |
| 8,691,268 B2 | 4/2014 | Weimann | |
| 8,697,112 B2 | 4/2014 | Dudnyk | |
| 9,925,087 B2 | 3/2018 | Bruder | |
| 2003/0044380 A1 | 3/2003 | Zhu | |
| 2008/0176262 A1 | 7/2008 | Kaplan | |
| 2012/0330210 A1 | 12/2012 | Yang | |
| 2013/0284186 A1* | 10/2013 | Touati | A61B 46/40 128/853 |
| 2014/0373851 A1 | 12/2014 | Powley | |
| 2018/0303967 A1* | 10/2018 | Quintero | A61L 24/04 |

\* cited by examiner

WOUND CLOSURE SYSTEMS FOR REDUCING SURGICAL SITE INFECTIONS COMPRISING INCISION DRAPES FILLED WITH RELEASABLE ANTIMICROBIAL AGENTS

FIELD OF THE INVENTION

The present invention relates to antimicrobial wound dressings, more specifically, the invention relates to antimicrobial incision drapes that release flowable anti-microbial agent onto the surgical instrument and edges of the incision and into the wound upon incising the drape.

BACKGROUND

Dressings play a major role in wound management, since the moist, warm and nutrient-rich environment of wound sites can provide conditions beneficial for microbial growth. Bacterial colonization and subsequent infection can interfere with the wound healing process by producing various substances (e.g., toxins, proteases and pro-inflammatory molecules) capable of inducing excessive and prolonged inflammatory responses. Antimicrobial dressings can be used against a range of bacteria such as methicillin-resistant *staphylococcus aureus* (MRSA), Gram-negative rods, and *Candida* species.

For infection prevention, maintaining sterility is of primary importance in surgical procedures, especially those involving incisions. Typically, the procedure for preventing surgical site infection includes showering, washing, shaving, scrubbing, prepping, and draping the surgical site. Each of these tasks is performed to prevent the introduction of pathogenic flora into the surgical site. However, the entire process for maintaining the sterility of the surgical site may be negated by e.g., occurrence of incising through a hair follicle. Hair follicles, no matter how well the skin is washed, scrubbed, and prepped, could be rich in bacteria. The act of making the surgical incision (i.e., incising) can release bacteria from hair follicles and other skin structures. Such small amounts of bacteria may be sufficient to cause a surgical site infection.

Furthermore, it may be beneficial to deliver other agents to a surgical incision such as: hemostatic agents to prevent or reduce bleeding, lubricants to facilitate surgical tools insertion, anti-inflammatory agents to reduce swelling and post-operative pain, chemotactic agents to accelerate capillary ingrowth post-surgery, wound healing agents and the like, and combinations thereof.

U.S. Patent Application Publication No. 20140373851, "Filled Incise Drape", discloses an article, comprising: a liquid impervious enclosure comprising: a first film layer; a second film layer, wherein the first film layer and the second film layer are hermetically sealed together to form at least one interior region enclosing an antimicrobial liquid composition; and a pressure sensitive adhesive layer disposed on an exterior surface of the first film layer.

PCT Patent Publication No. WO2017151226A1, "Drape for Use with Medical Therapy Systems", discloses a drape for medical applications, the drape comprising: a film layer having a first side and a second side; an adhesive layer coupled to the first side of the film layer, the adhesive layer having a first bond strength prior to application of the drape, a second bond strength in response to a force applied to the drape, and a third bond strength following exposure of the adhesive layer to electromagnetic radiation in a visible light spectrum; and a barrier layer releasably coupled to the second side of the film layer and configured to block at least a portion of the electromagnetic radiation in the visible light spectrum.

U.S. Pat. No. 4,643,181, "Antimicrobial Dressing or Drape Material", discloses a surgical dressing comprising a substrate coated on one surface with a solvent-based skin contact adhesive, said adhesive having a thickness of from 30 to 60 microns, particles of polyhexamethylene biguanide hydrochloride distributed through the adhesive, said particles having a size of from 20 to 300 microns.

U.S. Pat. No. 8,697,112, "Method for Treating a Surface with a Coating Comprising a Microencapsulated Therapeutic Agent and Device with Treated Surface", discloses a device comprising: a surface; a hydrophilic polymeric base layer comprising a hydrophilic polymer grafted to the surface; and a layer comprising microparticles of a therapeutic agent disposed on and complexed with the hydrophilic polymeric base layer.

U.S. Pat. No. 8,691,268, "Transdermal Delivery Using Encapsulated Agent Released by Ultrasound and/or Heat", discloses a portable transdermal drug delivery device consisting of: (A) a transdermal patch for infusing active substances into a user's body through the skin comprising: an inner disc, the inner disc including (i) encapsulated agents in microcapsules, wherein the microcapsules retain the encapsulated agents prior to activation by energy capable of rupturing the microcapsules and (ii) an external matrix or vehicle; and an outer disc for attachment of the patch to the skin of the user, thereby facilitating contact of the inner disc with a surface of the skin; (B) an activating probe attached to said transdermal patch and being equipped with a single multi-source element, wherein said multi-source element is comprised of multiple energy sources for providing ultrasound radiation or heat energy at different localized areas of said inner disc, wherein said activating probe is adapted for activating the transdermal patch by rupturing the microcapsules, thereby releasing said encapsulated agents into the external matrix or vehicle of the inner disc of said transdermal patch; and (C) a power supply for supplying energy to said multi-source element.

U.S. Pat. No. 3,598,123, "Bandage for Administering Drugs", discloses a medical bandage for use in the continuous administration to circulation of controlled quantities of systemically active drugs over a prolonged period of time by absorption through the external body skin or mucosa, said bandage comprising (1) a backing member bearing (2) a pressure-sensitive adhesive on one surface thereof, said pressure-sensitive adhesive having distributed therethrough (3) a plurality of discrete microcapsules, each of which microcapsules comprising a systemically active drug formulation confined within a wall member, said wall member being formed from drug release rate controlling material to continuously meter the flow of drug from the said microcapsules to the skin or mucosa at a controlled and predetermined rate over a prolonged period of time.

U.S. Pat. No. 9,925,087, "Wound and Therapy Compress and Dressing" discloses a dressing for treatment of a body part surface of a human or animal patient, the dressing comprising: a compress comprising a plurality of loose fill granules contained in an enclosure within the compress, the plurality of loose fill granules configured to deliver moist heat; a heat transmissive pad impregnated with an antibacterial medication, attached to a surface of the compress such that the heat transmissive pad is positioned between the compress and the body part surface, wherein the heat transmissive pad is activated by the moist heat delivered from the compress to release the antibacterial medication from the heat transmissive pad onto the body part surface; and wherein the fill granules substantially retain at least one antimicrobial metal material therein and allow repeated absorption and dissipation of moisture to and from the fill granules.

U.S. Patent Application Publication No. 20030044380A1, "Adhesive Including Medicament", discloses an adhesive for sealing a wound, the adhesive comprising a cyanoacrylate, a substance, and a defect forming agent, wherein the defect forming agent is capable of being removed from a cured cyanoacrylate matrix by solvation in an aqueous solution whereby a plurality of defects in the matrix are formed permitting release of the substance from the matrix at a controlled rate.

U.S. Pat. No. 6,139,856, "Composition Useful for Providing One-step Surgical Preparation and Drape", discloses a film forming composition for providing a protective coating on a skin surface, comprising: (a) about 30 to 60% by weight of solids selected from the group consisting of polyvinylidene diflouride and the copolymers thereof; (b) about 10 to 20% by weight of solids of a polymer of monomers selected from the group consisting of a lower alkylacrylate, a lower alkyl (meth)acrylate, a hydroxy lower alkylacrylate, an alpha beta unsaturated carboxylic acid having an acid number of about 20 to 150, and the copolymers thereof; (c) about 30 to 60% by weight of solids of a polymer of monomers selected from the group consisting of a dialkylaminoalkyl (meth)acrylate and, a lower alkyl (meth)acrylate; (d) about 0.5 to 2.0% of water based on total composition weight; (e) an effective amount of an antimicrobial lipid; and (f) an aqueous organic solvent for dissolving all components.

U.S. Pat. No. 4,654,256, "Article Containing Microencapsulated Materials", discloses an article comprising a thermoplastic polymeric substrate having rupturable microcapsules partially embedded therein.

U.S. Pat. No. 7,015,156, "Perfumed Abrasive Pad and Manufacturing Procedure", discloses an abrasive cleaning article that generates an aroma during use, said article comprising: a three-dimensional non-woven web of fibers; abrasive particles adhesively bonded to the fibers; and microcapsules including an aromatic substance adhesively bonded to the fibers, wherein the aromatic substance is released from the microcapsules during the normal use of the article to produce an aroma.

U.S. Pat. No. 3,691,271, "Sanitary Napkin having Homogeneously Distributed Microcapsules Filled with Delay Releasable Bactericidal and Fungicidal Deodorant", discloses a sanitary napkin consisting essentially of a body of an absorbent material of cellulose batting or layered paper or cotton fabric and a multiplicity of individual microcapsules enveloping effective amounts of a bactericidal and fungicidal deodorant agent, said microcapsules being homogeneously distributed in said cellulose batting or in alternating layers on said paper or cotton fabric, the size of each of said microcapsules ranging from 30-500 microns, the walls of said microcapsules being permeable or soluble on contact with the fluid associated with menstrual discharge whereby the release of said deodorant agent from said microcapsules in said sanitary napkin is delayed until contact with sufficient amounts of said fluid to permeate or solubilize the walls of said homogeneously distributed microcapsules, said walls of said microcapsules being made from a material selected from the group consisting of gelatin, ethyl cellulose, cellulose acetophthalate, polyvinyl alcohol and polyvinyl acetate and the density of said microcapsules being essentially equal to the density of said body of absorbent material.

PCT Patent Publication No. WO2012091457A2, "Antimicrobial Pad", discloses an antimicrobial pad comprising: polyurethane foam having pore voids of a predetermined size; and a microcapsule which containing antimicrobials therein and is provided to be encapsulated within the pore voids of the polyurethane foam to coat the surface of the polyurethane foam.

U.S. Pat. No. 3,490,454, "Catamenial Products having a Coating of Rupturable Microcapsules containing Medicants", discloses an absorbent catamenial device comprising an absorbent portion having a fluid-permeable wrapper, and having adhered to said absorbent portion at least one layer of a multiplicity of discrete rupturable microcapsules containing chemical materials capable of aiding in the control of the fluid associated with the menstrual discharge, said microcapsules. comprising minute encapsulated clusters of smaller individual microcapsules, the clusters being contained in shells of polymeric encapsulating materials.

U.S. Pat. No. 4,597,960, "Microencapsulated Astringent Hemostatic Agents and Methods of Use", discloses a granular composition for producing capillary hemostasis, comprising: a granular astringent hemostatic agent selected from the group consisting of ferric and aluminum inorganic salts encapsulated with a cellulose-based biocompatible polymer soluble in body fluids.

U.S. Pat. No. 5,717,005, "Adhesive Compositions and Products", discloses an adhesive composition, suitable for medical applications, comprising an adhesive having dispersed therein 2-10% by weight, based on the weight of the composition, of solid particles of chlorhexidine gluconate, wherein said particles have a particle size of less than 125μ and at least about 30% by volume of the particles have a particle size of not less than 5μ.

U.S. Patent Application Publication No. 20080176262, "Wound Dressing", discloses a method for determining the burden of metalloproteinases in biological tissues comprising: applying a diagnostic aid which has first material, which has a chemical composition that is degradable by a metalloproteinase, and a second material which is confined by the first material and which experiences changes in spectral properties; waiting an appropriate time for the metalloproteinases to degrade the first material; observing the spectral changes occurring with the second material; and assessing the burden of the metalloproteinases within the tissues.

U.S. Patent Application Publication No. 20120330210, "Antimicrobial Silicone-Based Wound Dressings", discloses a dressing comprising a silicone gel sheet, the silicone gel sheet comprising from about 95 wt. % to about 98 wt. % of a silicone elastomer and having dispersed therein (i) particulates of a chlorhexidine compound and (ii) at least one other antimicrobial, the total amount of chlorhexidine present in the gel sheet being up to 5 wt. %, the silicone elastomer crosslinked to an extent that provides sufficient cohesive strength to the dressing to allow for application and removal of the dressing from a surface while leaving minimal residue on the surface.

Some of the disclosures above relate to encapsulated microcapsules whereby only a few of these will be ruptured during the incision and therefore only a small portion of the therapeutic agent will be released, resulting in insufficient protection. Others relate to large fluid-filled pouches that will undesirably flood the wound with the therapeutic agent solutions, releasing a vast quantity of agent irrespective of the wound size/incision size. There is a need to create a drape that can aid with controlling and delivering antiseptics and other medicinal agents at and to the surgical site and to the surgical tools, during the surgical procedure, in controlled quantity and under controlled release.

SUMMARY OF THE INVENTION

In one embodiment, the present invention relates to a surgical incision drape comprising:

a substantially flat, flexible areal substrate having an upper side and an opposing tissue-facing side, a longitudinal axis and a pressure sensitive adhesive disposed on the tissue-facing side; and at least one hollow microtubular compartment containing a flowable medical agent, wherein said hollow microtubular compartment is positioned to intersect the longitudinal axis and is embedded into or positioned on the substrate.

In another embodiment, the invention relates to a method of using the drape of the foregoing embodiment, comprising the steps of:

positioning the drape on a tissue with the tissue-facing side facing towards the tissue and in contact with the tissue;

orienting the longitudinal axis generally along the expected incision line;

adhering the drape to the tissue via the pressure sensitive adhesive;

performing a surgical incision of the tissue through the drape, in the process cutting or severing at least one of the microtubular compartments thus opening at least one of the microtubular compartments; and allowing the agent to leach or ooze from the at least one microtubular compartment onto edges of a tissue wound formed by said incision.

In yet another embodiment, the invention relates to a surgical incision drape comprising:

a substantially flat, flexible areal substrate having an upper side and an opposing tissue-facing side, a longitudinal axis and a pressure sensitive adhesive disposed on the tissue-facing side; and a plurality of hollow microtubular compartments for receiving a medical agent, said microtubular compartments arranged side by side and positioned across the longitudinal axis so that each of said microtubular compartment cross the longitudinal axis and is embedded into or positioned on the substrate, wherein said microtubular compartments initially contain no medicinal agent and are connected to a peripheral channel which is distal from the longitudinal axis and generally parallel to the longitudinal axis and terminates with a port positioned on a periphery of said drape, said port configured to be connectable to a pressurized source of a medical agent.

DETAILED DESCRIPTION

Filled incision drapes that can deliver therapeutic agents at and to the surgical site are described herein. Exemplary embodiments of filled incision drapes of the present disclosure are generally comprised of liquid impervious microtubular compartments that encapsulate a flowable or fluid therapeutic agent, such compartments embedded into an adhesive patch or sheet used as a drape. Once applied to the surgical site and appropriately prepared, an incision can be made through the filled incision drape. Upon incising or otherwise puncturing through the filled incision drape, the therapeutic agent will be expressed from the drape and delivered into the incision. Embodiments of this invention enable the delivery of highly effective compositions of therapeutic agents typically not used after the initial incision in traditional surgery, because it would require an additional step, and bacteria from the incision is not typically recognized as a contributor to surgical infections. Filled incision drapes of this disclosure provide a single step for delivering a therapeutic agent directly to the surgical incision and to the surgical instrument as the incision is made.

Briefly, a surgical wound incision drape comprises an isolating patch or dressing or pad made of a flexible sheet of fabric, mesh, or non-woven material, that is adhesively and removably attached to the tissue in the area where tissue is about to be incised during surgical procedure. The drape is then cut through during surgery as the underlying tissue is being cut. Cutting through the drape opens up microcompartments filled with flowable anti-microbial agent containing fluid that is released in the area of the cut onto the surgical instrument (such as a surgical incision tool, saw, knife, scalpel, etc.) and onto the edge of the incision.

In a surgical wound incision drape of the present invention, an isolating patch/dressing/pad is adhesively attached to the tissue and then cut through during surgery, the drape material contains embedded elongated sealed compartments such as tubes which are filled with a liquid, flowable anti-microbial agent. The tubes are oriented generally across the cut axis of the drape so that they are cut through and opened during incision thus releasing the fluid agent along the cut, over the wound internal wall and over the scalpel, providing anti-bacterial action at the beginning and throughout surgery.

Advantageously, the release of the anti-infective medicant is proportional to the size of the incision, preventing excessive amounts of antimicrobial agent flooding the wound area. Advantageously, in some embodiments, the medicinal agent is released slowly and over time, thus providing necessary coverage during the procedure. Advantageously, all agent is available for release compared with systems with embedded microcapsules whereby only a small portion of the agent is released upon incising.

Figure 1A:
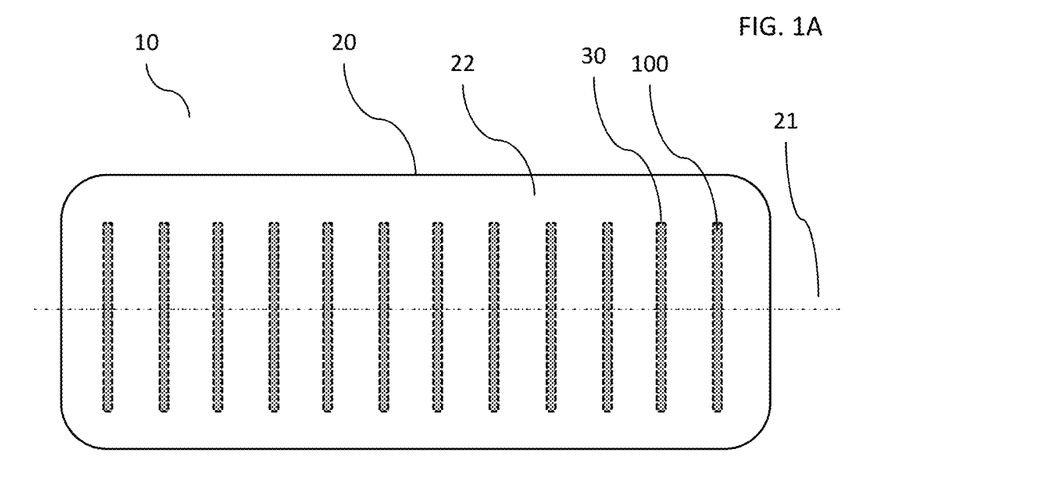
FIG. 1A shows an embodiment of an incision drape in a schematic top view.
Figure 1B:
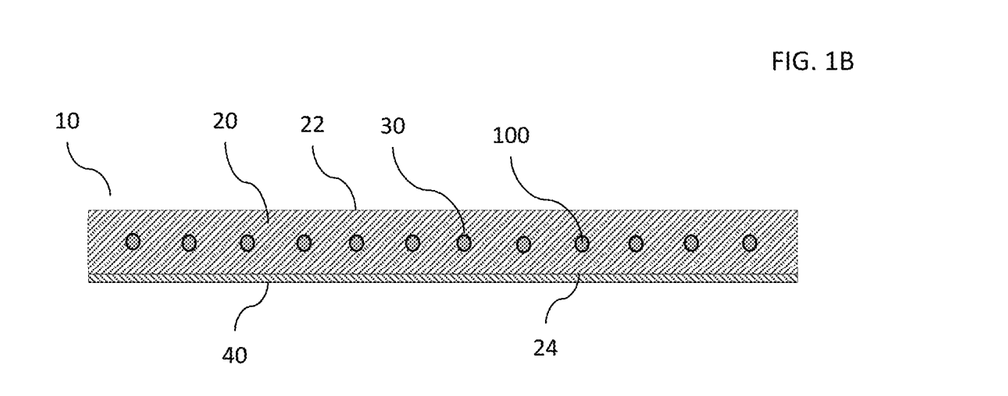
FIG. 1B shows an embodiment of an incision drape in a schematic side cross-sectional view.

Referring now to FIG. 1A, an embodiment of a drape 10 is shown in top view, with drape 10 comprising flat areal substrate 20 visible from the upper side 22 in FIG. 1A, with straight or linear closed microtubular compartments 30 containing liquid agent 100 embedded within substrate 20 and shown in dashed lines. Microtubular compartments 30 are positioned and oriented generally across longitudinal axis 21 of substrate 20, in other words across the expected surgical incision line, which generally can align with axis 21, with incision generally performed within the perimeter of substrate 20 and in the central area of substrate 20. At least a portion of microtubular compartments 30 is proximal and at least partially over longitudinal axis 21. Referring now to FIG. 1B, drape 10 is shown in side cross-sectional view, with upper side 22 facing upwards and tissue-facing side 24 facing downwards, with microtubular compartments 30 embedded within the substrate 20. On tissue-facing side 24 of substrate 20 is disposed adhesive 40, such as pressure-sensitive adhesive, which is configured for attachment to tissue prior to the surgical incision and removal after the surgical procedure. Adhesive 40 can be present as a continuous coating as shown, or applied in stripes, spots, dots, or any other shapes with some areas of tissue-facing side 24 free of adhesive 40.

Figure 1C:
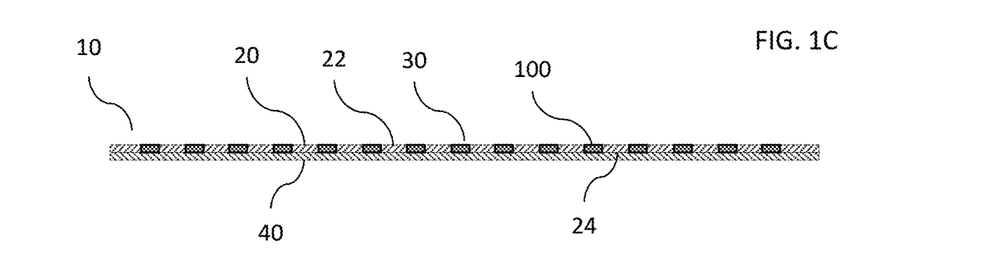
FIG. 1C shows an embodiment of an incision drape in a schematic side cross-sectional view with microtubular compartments comprising individual sealed microfluidic channels formed directly in substrate.

Referring now to FIG. 1C, drape 10 is shown in side cross-sectional view, with upper side 22 facing upwards and tissue-facing side 24 facing downwards, with microtubular compartments 30 comprising individual sealed microfluidic channels formed directly in substrate 20.

Figure 2:
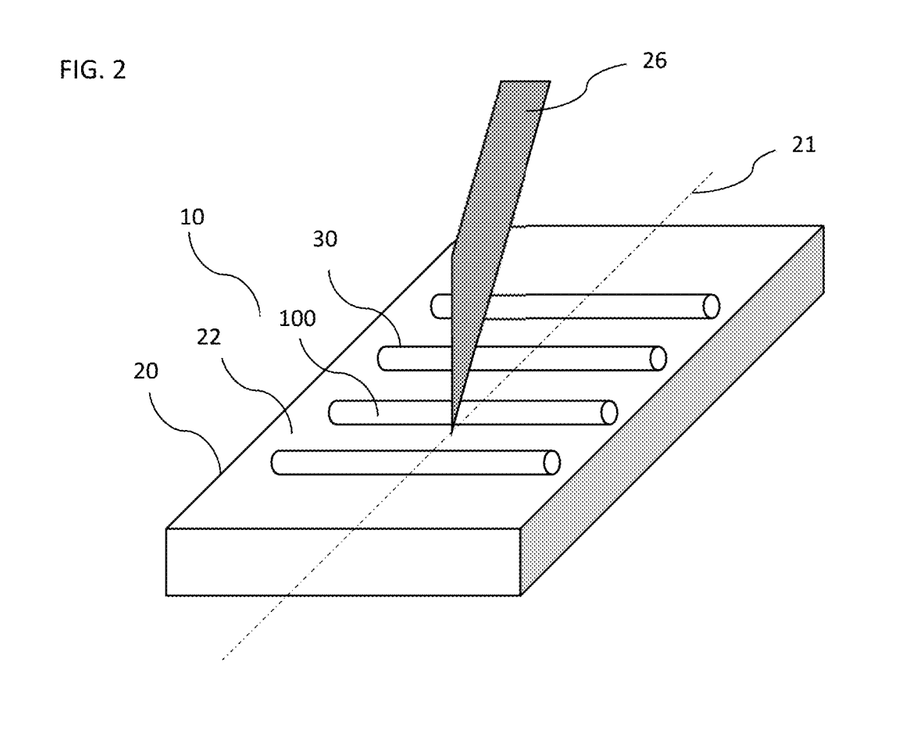
FIG. 2 shows an embodiment of an incision drape in a schematic perspective view prior to cutting through drape with a scalpel blade.

Referring to FIG. 2, showing a schematic perspective view, a scalpel blade 26 is shown in position prior to cutting through drape 10 along longitudinal axis 21 of substrate 20. In use, cutting though drape 10 and underlying tissue (not shown) will also cut through microtubular compartments 30 embedded within substrate 20 resulting in the instant or delayed release of liquid agent 100. Microtubular compartments 30 are configured to be frangible, severable, easily cuttable, or combinations thereof.

Advantageously, in this embodiment, only microtubular compartments 30 which are intersecting the cut performed by blade 26 will release agent 100. This results in release of the amount of agent proportional to the length of the cut. If all agent 100 from all microtubular compartments 30 was released into a relatively small cut that intersects only one microtubular compartment 30, resulting potentially in excessive amounts of agent 100 released, that could be detrimental due to flooding a relatively small wound area and resulting in an excess dose of anti-microbial agent. Thus in the shown embodiment the amount of agent released is proportional to the length of the cut.

Advantageously, in some embodiments, microtubular compartments 30 are configured to slowly release agent 100 from each cut microtubular compartment 30, with some fluid released instantly and some fluid released slowly over time supplying agent 100 to the wound edge. This is advantageously compared to embedding microcapsules in drape 10 that only able to release a very small amount of agent 100 from a small number of cut capsules in the line of incision, but not from other capsules, with no time delay effect as in the case of microtubular compartment 30. This is also advantageously compared to one large compartment in drape 10, which will release all agent 100 in response to even a short cut.

Figure 3:
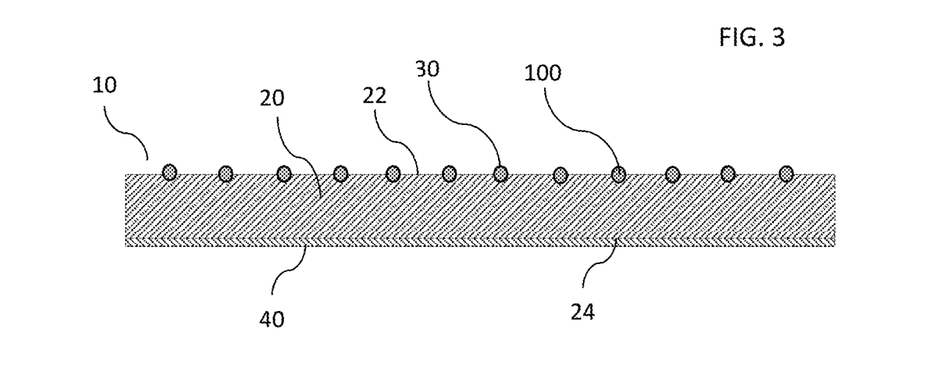
FIG. 3 shows an embodiment of an incision drape in a schematic side cross-sectional view.

Referring now to FIG. 3, an embodiment of drape 10 is shown in side cross-sectional view similar to FIG. 1B, with the embodiment shown different from FIG. 1B in that microtubular compartments 30 are located not in the bulk or in the middle of drape 10, but on the upper side 22.

Figure 4:
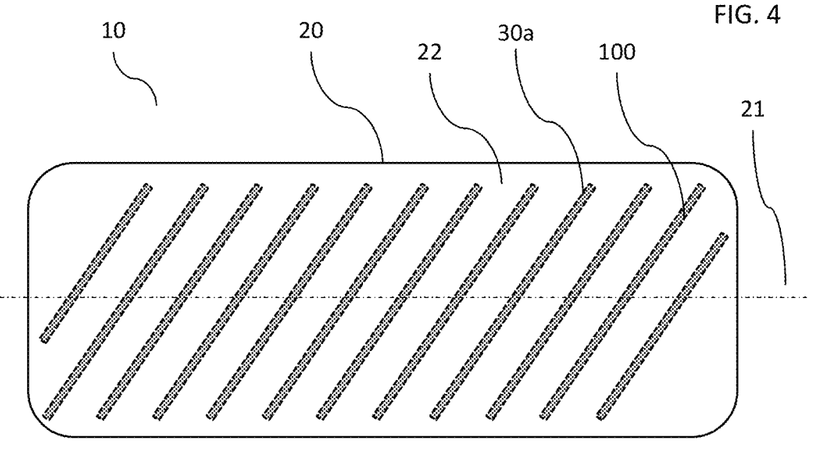
FIG. 4 shows an embodiment of an incision drape in a schematic top view.

Referring now to FIG. 4, an embodiment of drape 10 is shown in top view, with microtubular compartments 30a oriented generally not perpendicular and across longitudinal axis 21 of substrate 20, as in FIG. 1A, but under angle with respect to longitudinal axis 21 and still intersecting longitudinal axis 21 or the expected incision line. The angle between microtubular compartments 30a and longitudinal axis 21 is from about 20° to 70°, more preferably from about 30° to about 60°, most preferably about 45° as shown.

Figure 5:
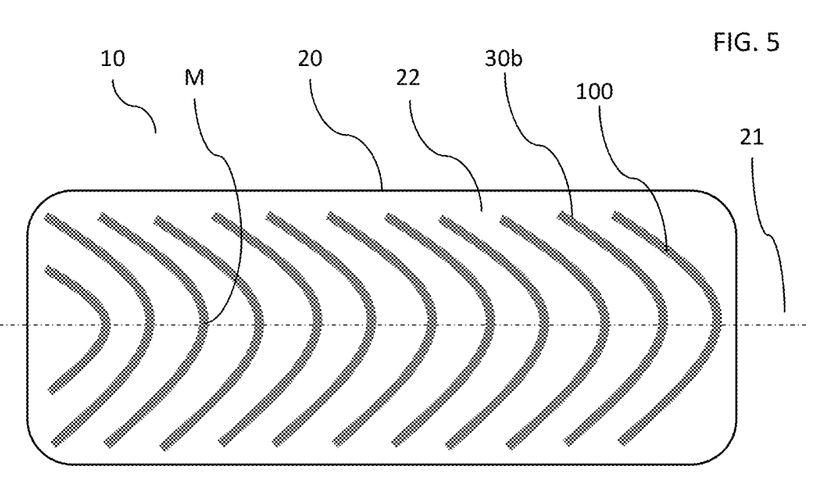
FIG. 5 shows an embodiment of an incision drape in a schematic top view.

Referring now to FIG. 5, an embodiment of drape 10 is shown in top view, with microtubular compartments 30b not linear as shown in embodiments of FIGS. 1A, 4, but "V" or "U" shaped and oriented generally across longitudinal axis 21 of substrate 20, with a mid-point "M" of the "V" or "U" shape being positioned approximately on longitudinal axis 21. This arrangement provides more agent 100 available for discharging, leaching, or oozing from each cut microtubular compartment 30b vs. microtubular compartments 30, 30a of other embodiments.

Figure 6:
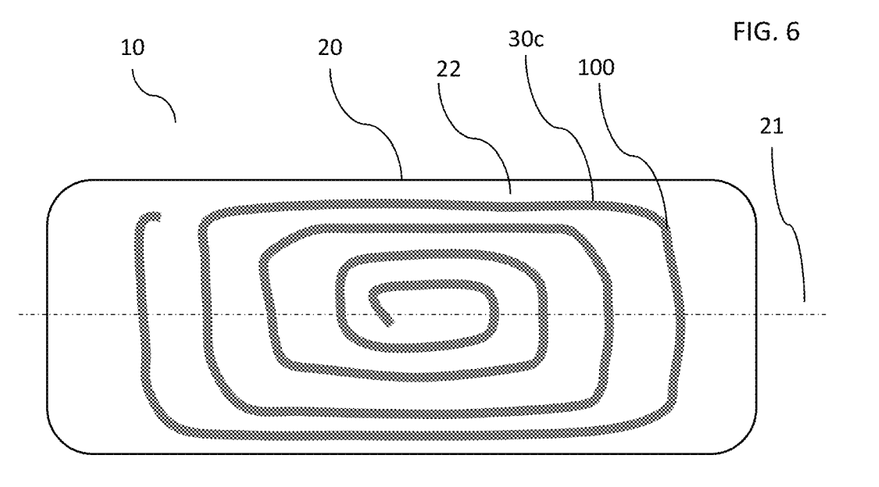
FIG. 6 shows an embodiment of an incision drape in a schematic top view.

Referring now to FIG. 6, an embodiment of drape 10 is shown in top view, with microtubular compartments 30c comprising one long generally spirally shaped microcompartment arranged over and across longitudinal axis 21 of substrate 20. This arrangement provides all agent 100 available for discharging, leaching, or oozing from the spiral-shaped microtubular compartment 30c when it is cut anywhere. Advantageously, the release is slow due to the distance agent 100 needs to travel through the microtubular compartment 30c to the area where the spiral-shaped microtubular compartment 30c was cut or severed. Spiral-shaped microtubular compartment 30c intersects longitudinal axis 21 at least 4 times, and up to 100 times, such as 9 times as shown in FIG. 6.

Figure 7:
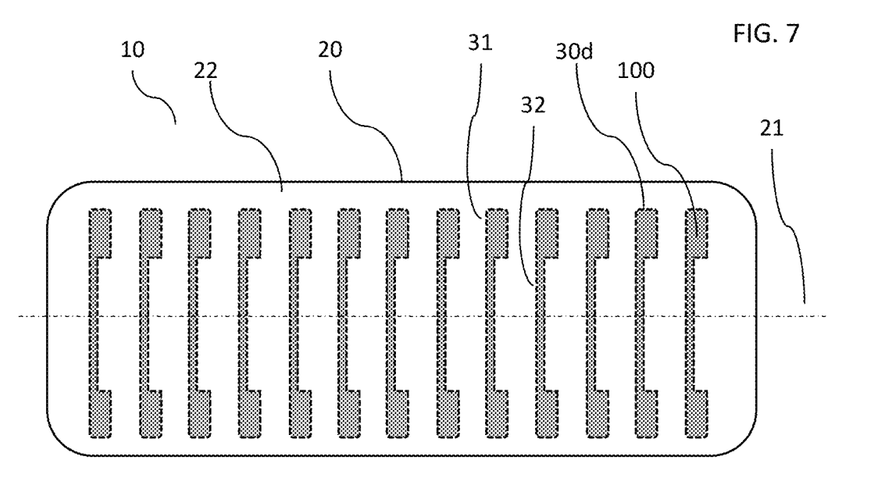
FIG. 7 shows an embodiment of an incision drape in a schematic top view.

Referring now to FIG. 7, an embodiment of drape 10 is shown in top view, with generally linear microtubular compartments 30d positioned across/perpendicular longitudinal axis 21 of substrate 20 similar to embodiment of FIG. 1A. Microtubular compartments 30d have capillary central portion 32 of smaller diameter which is proximal and at least partially over longitudinal axis 21. Microtubular compartments 30d have larger volume (such as larger diameter) peripheral portion 31 which is distal from longitudinal axis 21. In the embodiment shown, there are two peripheral portions 31 arranged on either side of capillary central portion 32. This arrangement provides more agent 100 available for discharging from each cut microtubular compartment 30d, but with a slow leaching or oozing of agent 100 due to smaller diameter capillary central portion 32. Peripheral portion 31 can be of linear and rectangular shape, cylindrical shape, spherical balloon-like shape or generally of any suitable geometry to provide repository for additional agent 100 for leaching through a cut capillary central portion 32.

In an alternative embodiment (not shown), there is only one peripheral portion 31 arranged on one side of capillary central portion 32.

Figure 8:
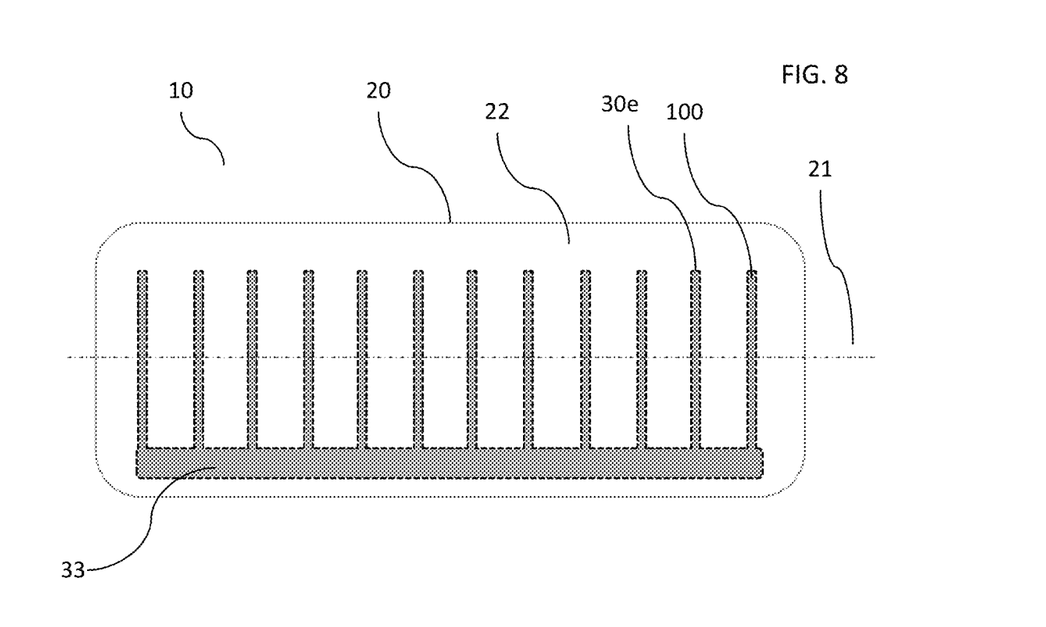
FIG. 8 shows an embodiment of an incision drape in a schematic top view.

Referring now to FIG. 8, an embodiment of drape 10 is shown in top view, with microtubular compartments 30e linear-shaped and positioned across/perpendicular longitudinal axis 21 of substrate 20 similar to embodiment of FIG. 1A. Microtubular compartments 30e are all connected to a larger diameter peripheral channel 33 which is distal from and generally parallel to longitudinal axis 21.

In the embodiment shown, there is one peripheral channel 33 arranged on one side of substrate 20. This arrangement provides more agent 100 available for discharging from each cut microtubular compartment 30e, but with a slow leaching or oozing of agent 100 due to smaller diameter capillary central portion 32. Peripheral channel 33 can be of linear and rectangular shape, cylindrical shape, spherical balloon-like shape or generally of any suitable geometry to provide repository for additional agent 100 for leaching through severed or cut microtubular compartments 30e. In an alternative embodiment (not shown), there are two peripheral channels 33 on each side of substrate 20 which are located on periphery of substrate 20, distal from and generally parallel to longitudinal axis 21.

Figure 9:
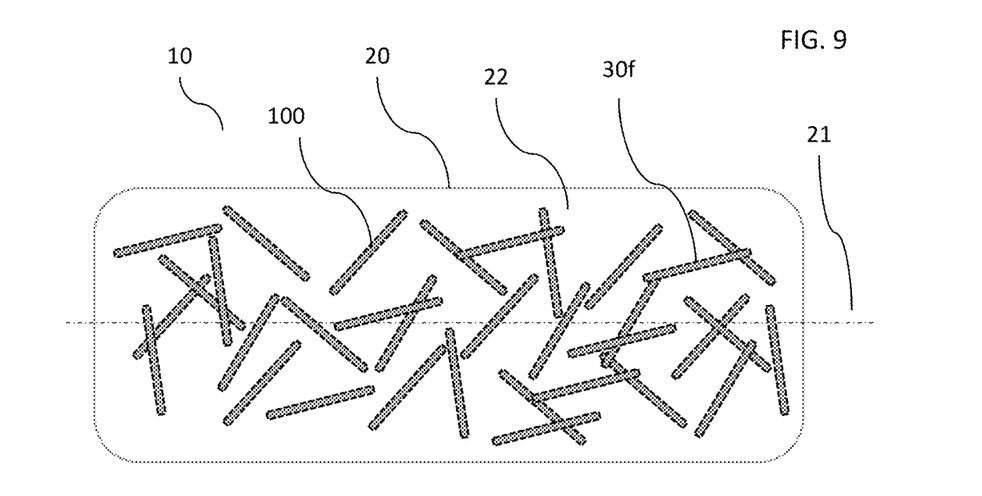
FIG. 9 shows an embodiment of an incision drape in a schematic top view.

Referring now to FIG. 9, an embodiment of drape 10 is shown in top view, with microtubular compartments 30f randomly distributed throughout substrate 20, with at least some intersecting longitudinal axis 21. Advantageously, in this embodiment, cutting through drape 10 in any direction will result in release of agent 100.

Figure 10:
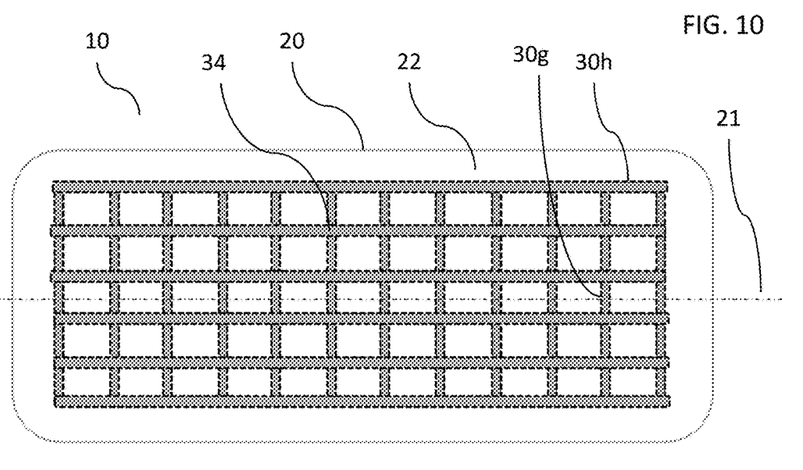
FIG. 10 shows an embodiment of an incision drape in a schematic top view.

Referring now to FIG. 10, an embodiment of drape 10 is shown in top view, with microtubular compartments 30g arranged perpendicular to microtubular compartments 30h, which are parallel to longitudinal axis 21, forming substantially square grid. In one embodiment, microtubular compartments 30g, 30f are connected to each other at each intersection point 34. In another embodiment, microtubular compartments 30g, 30f are not connected to to each other at each intersection point, such as by being positioned in different planes within substrate 20. Advantageously, cutting of drape 10 in any direction will intersect certain microtubular compartments 30g, 30f resulting in release of agent 100 along the cut and in the cut.

Figure 11A:
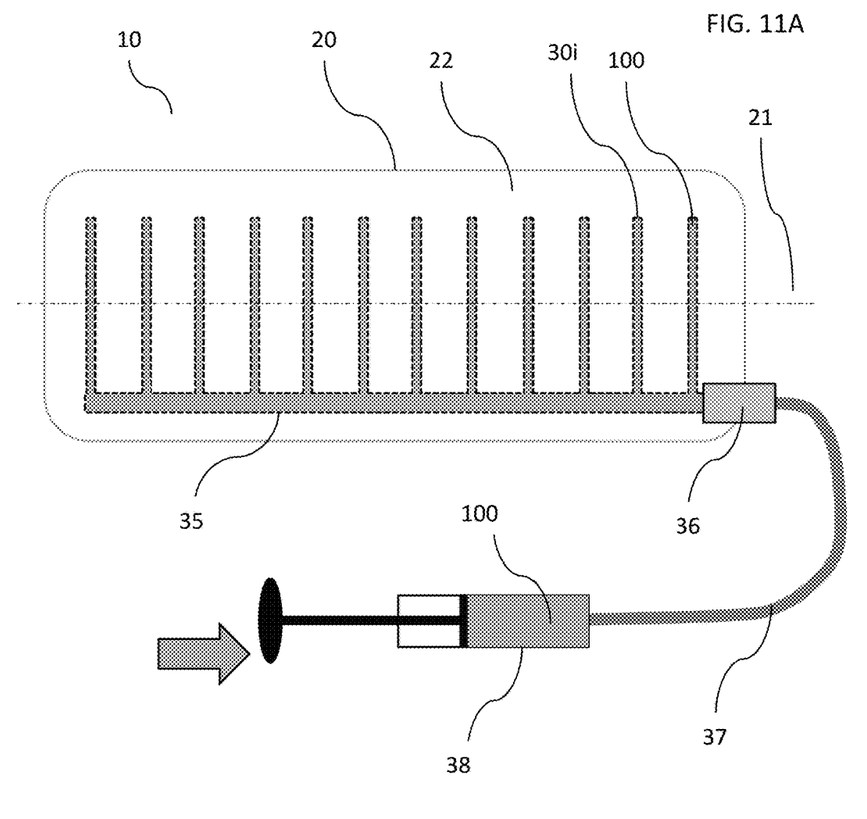
FIG. 11A shows an embodiment of an incision drape in a schematic top view and connected via cannula to a source of pressurized agent.

Referring now to FIG. 11A, an embodiment of drape 10 is shown in top view, with microtubular compartments 30i linearly shaped and positioned across or perpendicular longitudinal axis 21 of substrate 20 similar to embodiment of FIG. 1A. Microtubular compartments 30i are connected to a peripheral channel 35 which is distal from and generally parallel to longitudinal axis 21 and located on periphery of substrate 20, and terminates in a port 36 positioned on a periphery of drape 10. Peripheral channel 35 can be of linear or rectangular shape, cylindrical shape, or generally of any suitable geometry to provide for delivery of agent 100 to microtubular compartments 30i.

Port 36 is shown connected via cannula 37 to source of pressurized agent 100, such as a pump, which in one embodiment can be, as shown, a syringe 38. Alternatively, any pump 38 can be used, including a pump comprising a hydrostatic pressure source, i.e. elevated source (not shown) of agent 100, which is positioned higher that drape 10, to enable gravity-driven flow. Other pumps can include low volumetric flow peristaltic pumps, piston pumps, elastic bulbs and similar. In one embodiment (not shown) pump 38 comprises a pressurized container.

Pressurizing agent 100 in pump 38 as indicated by arrow in FIG. 11A, delivers agent 100, as needed, to the edges of the wound after drape 10 and corresponding microtubular compartments 30i are cut.

Figure 11B:
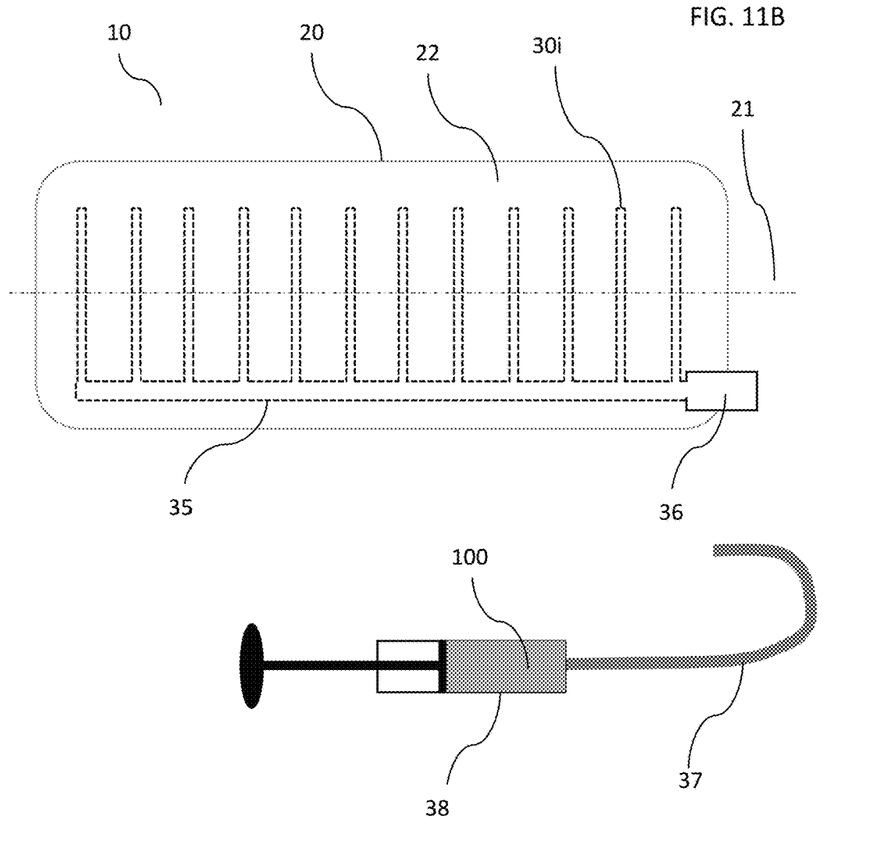
FIG. 11B shows an embodiment of an incision drape in a schematic top view and having no medicinal agent prior to connection via cannula to a source of pressurized agent.

In some embodiments, as shown in FIG. 11B, drape 10 is supplied with no agent 10 inside. After applying drape 10 to the tissue, pressurized agent 100 is supplied to drape 10 via cannula 37 by connecting to port 36 preferably before cutting of drape 10. In this embodiment, a selection of agent 100 can be made based on a specific need and area of tissue, patient needs, risks, etc. Advantageously, there can be a change in the supplied agent 100 from one agent another agent (such as different types of agents or different concentration of agents), intraoperatively, as needed.

Figure 12:
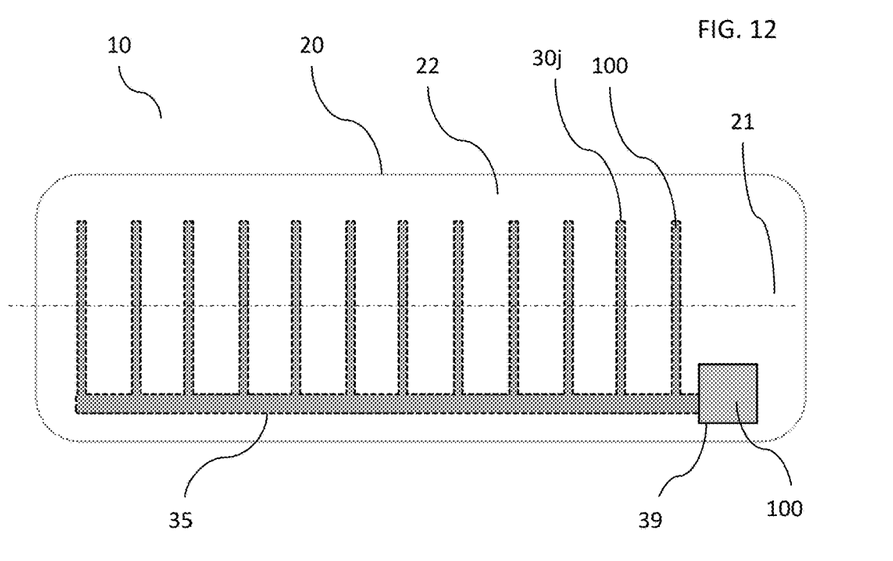
FIG. 12 shows an embodiment of an incision drape in a schematic top view.

Referring now to FIG. 12, an embodiment of drape 10 is shown in top view, with microtubular compartments 30j linearly shaped and positioned across/perpendicular longitudinal axis 21 of substrate 20 similar to embodiment of FIG. 1A. Microtubular compartments 30i are connected to peripheral channel 35 which is distal from and generally parallel to longitudinal axis 21 and located on periphery of substrate 20 and terminates in a hollow bulb 39 positioned on a periphery of drape 10 and containing agent 100. In one embodiment, bulb 39 is elastic and contains agent 100 under pressure. Pressurized agent 100 in bulb 39 is delivered to the edges of the wound after drape 10 and corresponding microtubular compartments 30j are cut or severed. In another embodiment, manual compression of bulb 39 is facilitating additional flow of agent 100 through microtubular compartments 30j that are cut or severed.

Figure 13:
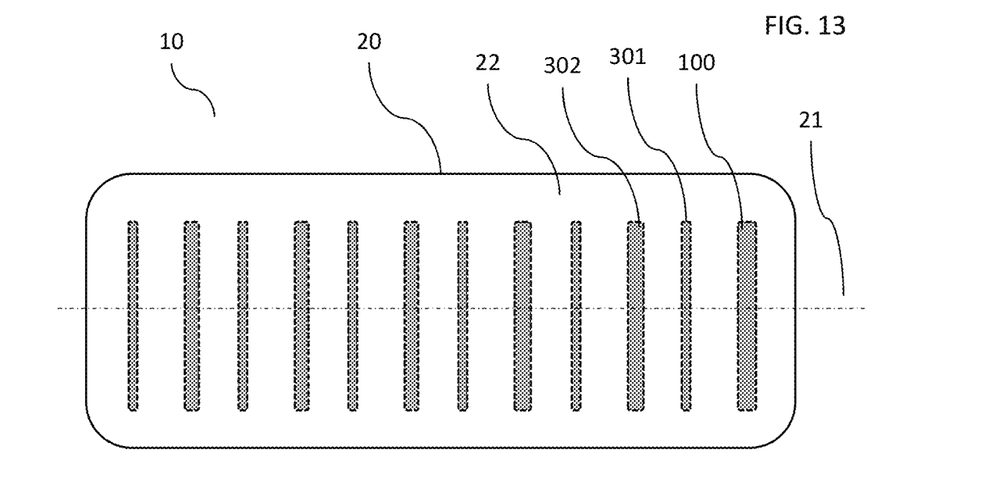
FIG. 13 shows an embodiment of an incision drape in a schematic top view.

In some embodiments, and referring to FIG. 13, showing a schematic top view of an embodiment of drape 10, microtubular compartments present are of two or more types, with microtubular compartments 301 with smaller diameter having slower or delayed release of agent 100, and microtubular compartments 302 with larger diameter having faster release of agent 100 upon severing or cutting microtubular compartments 301, 302. As shown, majority of microtubular compartments of different types are preferably interspersed or disposed interdigitated so that microtubular compartments 301 of the first type are surrounded by microtubular compartments 302 of the second type and mutatis mutandis microtubular compartments 302 of the second type are surrounded by microtubular compartments 301 of the first type. Such arrangement results in immediate release of agent 100 from microtubular compartments 302, and sustained release of agent 100 during surgical procedure thereafter from microtubular compartments 301.

Figure 14:
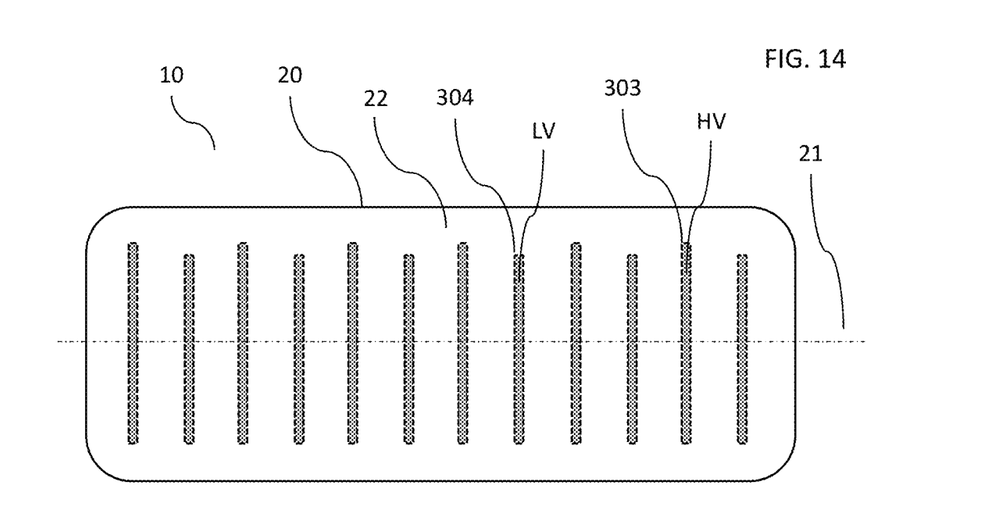
FIG. 14 shows an embodiment of an incision drape in a schematic top view.

In some embodiments, and referring to FIG. 14, microtubular compartments present are of two or more types, with microtubular compartments 303 having higher viscosity agent 100 formulation (indicated by letters "HV" in FIG. 14) and thus having slower or delayed release of agent 100, and microtubular compartments 304 (shown slightly shorter in FIG. 14 for easier identification) having lower viscosity agent 100 formulation (indicated by letters "LV" in FIG. 14) and thus having faster or instant release of agent 100 upon severing or cutting microtubular compartments. As shown, microtubular compartments of different types are preferably interspersed or disposed interdigitally so that most microtubular compartments 303 are surrounded by microtubular compartments 304 of the second type and mutatis mutandis most microtubular compartments 304 of the second type are surrounded by microtubular compartments 303 of the first type. Such arrangement results in immediate release of agent 100 from microtubular compartments 304, and sustained release of agent 100 during surgical procedure thereafter from microtubular compartments 303.

Figure 15:
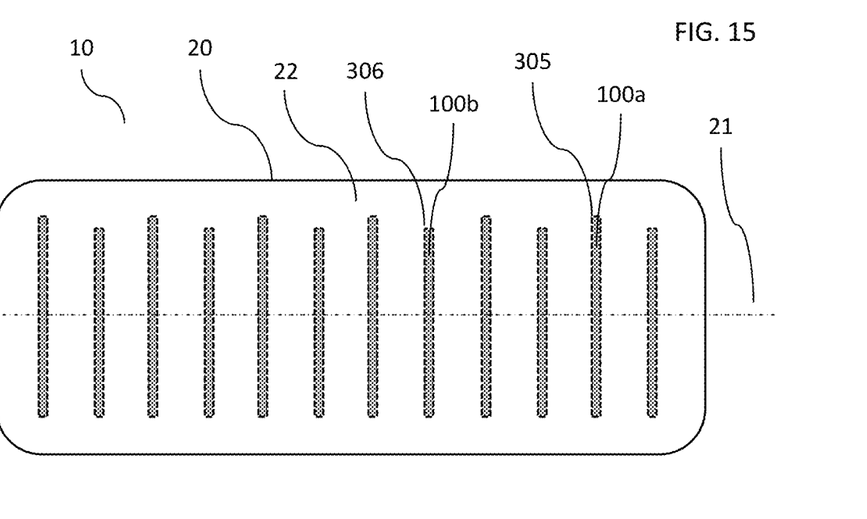
FIG. 15 shows an embodiment of an incision drape in a schematic top view.

In some embodiments, and referring to FIG. 15, microtubular compartments present are of two or more types, and having the same diameters (as shown) or different diameters (not shown, but similar to embodiments of FIG. 13), with microtubular compartments 305 (shown slightly longer in FIG. 15 for easier identification) containing a first agent 100a, and microtubular compartments 306 containing a second agent 100b. Having two or more agents 100a, 100b in separate compartments simplifies storage for incompatible agents which can be active against different microorganisms, such as gram-negative and gram-positive bacteria.

While release of agent 100a, 100b can be simultaneous, in some embodiments, the release is performed with a different profile, such as when agent 100a is released instantly or within first 3-30 seconds, and agent 100b is released slower via delayed release. Delayed release can be achieved by diameters of microtubular compartments as was illustrated above, and/or by formulating viscosity of agent 100a, 100b with excipients and diluents, with higher viscosity resulting in delayed or slower release as was illustrated above.

As shown, microtubular compartments of different types are preferably interspersed or disposed interdigitated so that most microtubular compartments 305 of the first type are surrounded by microtubular compartments 306 of the second type and mutatis mutandis most microtubular compartments 306 of the second type are surrounded by microtubular compartments 305 of the first type. Such arrangement results in release of both agent 100a, 100b upon severing or cutting microtubular compartments.

Figure 16A:
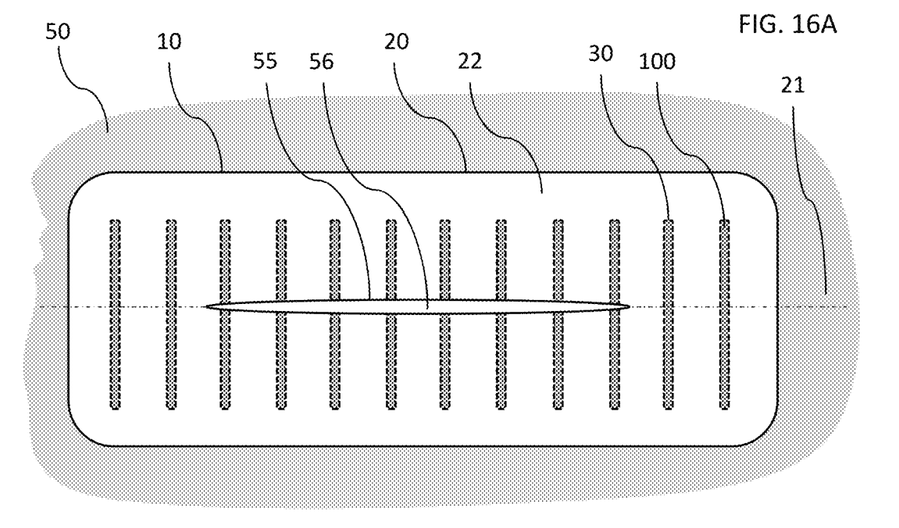
FIG. 16A shows an embodiment of an incision drape in a schematic top view in use positioned on a tissue.
Figure 16B:
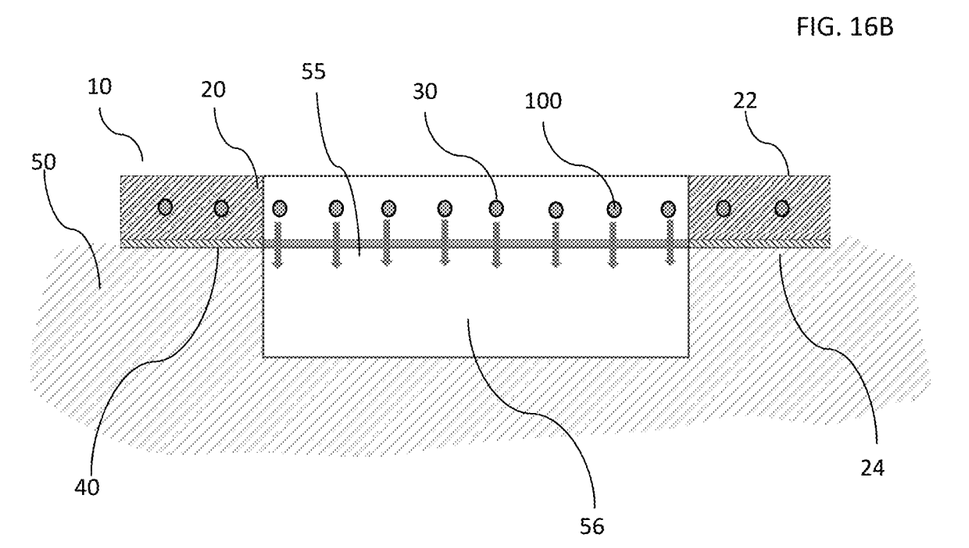
FIG. 16B shows an embodiment of an incision drape in a schematic side cross-sectional view in use positioned on a tissue.

In use, and referring to FIGS. 16A, 16B, drape 10 is positioned on tissue 50 and adhered to tissue 50, with upper side 22 facing upwards and tissue-facing side 24 facing downwards towards tissue 50 and in contact with tissue 50. Longitudinal axis 21 of substrate 20 is oriented generally along the expected incision line. Tissue-facing side 24 of substrate 20 is adhered to tissue 50 via adhesive 40.

Surgical incision 55 of tissue 50 is then performed through drape 10, in the process cutting or severing at least one of microtubular compartments 30. Opening of microtubular compartments 30 along the cut line or edge 55 of the wound 56 enables agent 100 to leach or ooze from microtubular compartments 30 onto the sides of the surgical instrument (not shown) and onto edges 55 of wound 56 and partially into the wound 56 as schematically shown by arrows in FIG. 16B.

In some embodiments, microtubular compartments 30 are collapsible. In some embodiments, microtubular compartments 30 are elastic and pressurized. In some embodiments, microtubular compartments 30 are configured for collapsing when manually pressed through substrate 20.

In some embodiments, the release or leaching/oozing of all or up to about 80% of agent 100 from microtubular compartments 30 is configured for release within about 3 to 10 seconds after cutting or severing microtubular compartments 30, such as within 5 to 10 seconds. In alternative embodiments, the release of all or up to 80% of agent 100 is occurring over extended period such as from 10 to 600 seconds and up to 10 hours.

In some embodiments, the release of about 40-60% of agent 100 occurs very quickly, i.e. within 10 seconds, and the rest is slowly released over about 30 to 600 seconds (10 min), or up to about 6000 seconds (100 min) or up to 10 hours.

Dimensions

Microtubular compartments can have inner diameters ranging from about 0.15 mm to about 2 mm, more preferably 0.2 mm to 1 mm, such as 0.3, 0.5, 1 mm. Microtubular compartments can also have rectangular, oval, etc. cross-section, with a similar cross-sectional area. The length of microtubular compartments is from about 10 mm to about 500 mm, such as 15, 20, 30, 50, 75, 100 mm. The wall thickness of microtubular compartments is from about 0.05 mm to about 1 mm, such as 0.1, 0.3, 0.5 mm.

The number of microtubular compartments can vary from 1 for spiral embodiment to about from 10-500, such as 8, 12, 20, 30, 40, 50, 80, 100.

Substrate 20 can have any geometric shape, including rectangular, oval, square, or similar.

The length of substrate 20 is from about 5 cm to about 300 cm, such as 10, 15, 20, 25 cm. The width of substrate 20 is from about 2 cm to about 300 cm, such as 3, 5, 10, 15, 20, 25 cm. The thickness of substrate 20 is from about 0.5 mm to about 5 mm, such as 1, 2, 3 mm.

Materials

Substrate 20 materials may be any polymetric materials, which are inert and/or biocompatible, such as polyethylene, polypropylene, polyesters, oxidized regenerated cellulose (ORC), chitosan, collagen, gelatin, and similar, and combinations thereof. Substrate 20 can be molded or extruded sheet, woven fabric, non-woven felt, or combinations thereof. In one embodiment, substrate 20 comprises a wicking material that is able to distribute agent 100 from discrete microtubular compartments for release over the whole area of drape that is cut.

Microtubular compartments 30 materials are any polymetric materials, which are biocompatible and stable in contact with agent 100, such as polyethylene, polypropylene, polyesters, and similar.

Flowable medicant or medicinal agent 100 comprises liquid or semi-liquid formulations containing a diluent and at least one anti-microbial and/or anti-infective and/or, antiseptic agent. The diluent can be any fluid, such as water, saline, ethanol, etc., and combinations thereof. The agent can be a natural or synthetic agent suitable for topical application on wounds, skin, mucosa, or cavities, a Topical Anti-Infective Agent, having therapeutic or prophylactic antibiotic properties against infectious viral, bacterial, or protozoal agents by inhibiting growth and survival of such organisms.

The agent can be ethanol, triclosan, chlorhexidine gluconate (CHG), polyhexamethylene biguanide, antibiotic, such as gentamicin, and or fluoroquinolone antibiotics, including ciprofloxacin, ofloxacin, and norfloxacin, etc. A number of agents suitable for use with the present invention are known to a skilled artisan, including 3,6-Diamino-10-methylacridinium Chloride; 8-Hydroxyquinoline product; 8-Hydroxyquinoline Sulfate Ointment; Acriflavine product; Acrisorcin; Actinoquinol; Alexidine; Aluminum acetate; Ambazone; Aminacrine hydrochloride; Aminacrine product; Aminacrine Pyruvate; Aminacrine Undecylate; Amphomycin Calcium; Amylmetacresol; Auriclosene; Azelaic acid; Bensalan; Benzalkonium product; Benzethonium chloride; Benzethonium product; Benzododecinium; Benzododecinium bromide; Benzoin; Benzoxiquine; Benzoxonium Chloride; Benzoyl peroxide; Benzyl alcohol; Benzylsulfamide; Bibrocathol; Biclotymol; Bismuth subgallate; Bismuth Tribromophenate; Boric acid; Calcium hydroxide; Camphor product; Carbamide peroxide; Cetalkonium; Cetalkonium chloride; Cetrimonium; Cetrimonium Chloride; Cetylpyridinium Acetate; Cetylpyridinium Bromide; Cetylpyridinium chloride; Cetylpyridinium Chloride Anhydrous; Cetylpyridinium product; Chaulmosulfone; Chloramine-T; Chlorhexidine gluconate; Chlorhexidine hydrochloride; Chlorhexidine product; Chlorindanol; Chloroazodin; Chlorocresol; Chlorothymol; Chloroxylenol; Chlorphenesin product; Chlorphenoctium Amsonate; Cicliomenol; Cinoquidox; Cloflucarban; Cloguanamil; Cloponone; Cocamidopropylbetaine (in water); Crotamiton; Crotoniazide; Cuprimyxin; Cyclomenol; Dakins Solution; Debropol; Decominol; Deditonium; Deditonium Bromide; Dibromopropamidine product; Dichlorobenzyl alcohol; Dichloroxylenol; Dicresulene; Dipyrithione; Disiquonium; Disiquonium Chloride; Dodeclonium bromide; Dofamium; Dofamium Chloride; Famiraprinium Chloride; Fenticlor product; Fepradinol; Fludazonium; Fludazonium Chloride; Fluorosalan; Furmethoxadone; Gloxazone; Guaiacol product; Halazone; Halopenium Chloride; Haloprogin; Hexachlorophene product; Hexedine; Hexetidine product; Hexylresorcinol product; Hydrogen peroxide; Iodoform; Laurcetium; Laurcetium Bromide; Laurixamine; Lauroguadine; Laurolinium Acetate; Lopobutan; Mafenide acetate; Mecetronium; Mecetronium ethylsulfate; Mequidox; Meralein; Merbromin product; Mercurous iodide; Mercury ammonium chloride product; Metabromsalan; Methaniazide; Methylisothiazolinone; Monalazone; Monalazone Disodium; Morniflumate; Myristalkonium Chloride; Nibroxane; Nifuradene; Nifuraldezone; Nifuralide; Nifurethazone; Nifurfoline; Nifurimide; Nifurizone; Nifuroquine; Nifuroxazide; Nifuroxime; Nifurpirinol; Nifurprazine; Nifurvidine; Nifurzide; Nitromersol; Noxythiolin product; Octafonium Chloride; Octenidine Saccharin; Olanexidine; Opratonium Iodide; Oxyquinoline sulfate; Parachlorophenol; Penoctonium; Penoctonium Bromide; Phanquone; Phenolate Sodium; Phenoxyethanol product; Phenyl ethyl alcohol; Phthalylsulfacetamide; Picloxydine; Picric acid; Pirralkonium; Pirralkonium Bromide; Pirtenidine; Pirtenidine Hydrochloride; Prednicarbate; Proflavine Dihydrochloride; Proflavine Hemisulfate; Proflavine product; Proflavine Sulfate; Resorcinol; Resorcinol Monoacetate; Romifenone; Salicylanilide; Sanguinarium Chloride; Selenium sulfide; Sepazonium; Sepazonium Chloride; Silver nitrate; Silver Oxide; Silver Picrate; Silver sulfadiazine; Sodium meralein; Sulfacecole; Sulfarsphenamine; Symclosene; Talmetoprim; Tavaborole; Temodox; Tetradonium; Tetradonium Bromide; Thimerosal product; Thymol iodide; Thymol product; Tibezonium; Tibezonium Iodide; Toliodium; Toliodium Chloride; Tribromsalan; Trichlorocarbanilide product; Undecoylium Chloride; Zinc Carbonate; Zinc phenolsulfonate;

Pressure sensitive adhesive (PSA) materials are known to these skilled in the art, and can include, for instance, one of the following: hydrocolloids; homo-polymer emulsion (PVA); water-based acrylic adhesives; polyurethane dispersions (PUDs); polyethylene glycol; dextrin/starch-based adhesives; N-vinyl caprolactam homopolymers; N-vinyl pyrrolidone copolymers; polyvinyl alcohol; cellulose ethers; methylcellulose; carboxymethylcellulose; polyvinylpyrrolidone; polyvinyl acetates, non-water based acrylic adhesives; cyanoacrylate adhesives; epoxy; silicone based adhesives; urethane, and similar, and combinations thereof.

It should be understood that the foregoing disclosure and description of the embodiments of the present invention are illustrative and explanatory thereof and various changes in the size, shape and materials as well as in the description of the preferred embodiment may be made without departing from the spirit of the invention.

We claim:

1. A surgical incision drape, comprising:
   a substantially flat, flexible areal substrate having an upper side and an opposing tissue-facing side, a longitudinal axis and a pressure sensitive adhesive disposed on the tissue-facing side; and
   at least one hollow microtubular compartment containing a flowable medical agent, wherein said hollow microtubular compartment is positioned to intersect the longitudinal axis and is embedded into or positioned on the substrate;
   wherein said at least one hollow microtubular compartment is frangible;
   wherein said at least one hollow microtubular compartment is a plurality of hollow microtubular compartments arranged side by side with respect to the longitudinal axis and positioned across the longitudinal axis so that each of said hollow microtubular compartments crosses the longitudinal axis.

2. The surgical incision drape of claim 1, wherein said plurality of hollow microtubular compartments is arranged in a spiral configuration and is crossing said longitudinal axis at least 4 times.

3. The surgical incision drape of claim 1, wherein said plurality of hollow microtubule compartments comprises at least eight hollow microtubular compartments.

4. The surgical incision drape of claim 1, wherein said plurality of hollow microtubular compartments is linear, angular, U-shaped, or V-shaped.

5. The surgical incision drape of claim 1, wherein said plurality of hollow microtubular compartments comprise:
   a capillary central portion having a smaller diameter, said capillary central portion proximal and at least partially over the longitudinal axis, and
   a larger diameter peripheral portion which is distal from the longitudinal axis.

6. The surgical incision drape of claim 1, wherein said plurality of hollow microtubular compartments are all connected together to a peripheral channel which is distal from the longitudinal axis and generally parallel to the longitudinal axis.

7. The surgical incision drape of claim 1, wherein said surgical incision drape further comprises a second plurality of hollow microtubular compartments that do not intersect the longitudinal axis and are interconnected with said plurality of hollow microtubular compartments forming a grid.

8. The surgical incision drape of claim 6, wherein said peripheral channel terminates in a bulb positioned on a periphery of said surgical incision drape and containing said flowable medical agent,
   wherein said bulb is elastic and contains said flowable medical agent under pressure.

9. The surgical incision drape of claim 1, wherein said plurality of hollow microtubular compartments comprise:
   a smaller diameter microtubular compartments configured for slow release of the flowable medical agent;
   and a larger diameter microtubular compartments configured for faster release of the flowable medical agent,
   wherein said smaller diameter microtubular compartments are interspersed or disposed interdigitally with said larger diameter microtubular compartments.

10. The surgical incision drape of claim 1, wherein said plurality of hollow microtubular compartments comprise:
- a first type microtubular compartments containing a high viscosity formulation of said flowable medical agent and configured for slow release of the flowable medical agent;
- and a second type microtubular compartments containing a low viscosity formulation of said flowable medical agent and configured for fast release of the flowable medical agent;
- wherein said first and second type microtubular compartments are interspersed or disposed interdigitally with each other.

11. The surgical incision drape of claim 1, wherein said plurality of hollow microtubular compartments comprise:
- a first type microtubular compartments containing a first agent; and a second type microtubular compartments containing a second agent;
- wherein said first and second type microtubular compartments are interspersed or disposed interdigitally with each other.

12. The surgical incision drape of claim 11, wherein said first type microtubular compartments containing the first agent are configured for fast release of the first agent;
- and the second type microtubular compartments containing the second agent are configured for slow release of the second agent.

13. A method of using the surgical incision drape of claim 1, comprising the steps of:
- positioning the surgical incision drape on a tissue with the tissue-facing side facing towards the tissue and in contact with the tissue;
- orienting the longitudinal axis generally along the expected incision line;
- adhering the surgical incision drape to the tissue via the pressure sensitive adhesive;
- performing a surgical incision of the tissue through the surgical incision drape, in the process cutting or severing at least one of the plurality of hollow microtubular compartments thus opening at least one of the plurality of hollow microtubular compartments; and
- allowing the flowable medical agent to leach or ooze from at least one of the plurality of hollow microtubular compartments onto edges of a tissue wound formed by said incision.

14. The method of claim 13, wherein leaching or oozing of up to 80% of the flowable medical agent from the at least one microtubular compartment is configured for release within 3 to 600 seconds.

15. The surgical incision drape of claim 1, wherein said flowable medical agent comprises antimicrobial agent, antibacterial agent, antibiotic, antiviral, triclosan, chlorohexidine gluconate, polyhexamethylene biguanide, or combinations thereof.

16. The surgical incision drape of claim 1, wherein said plurality of hollow microtubular compartments comprise individual sealed microfluidic channels formed directly in said substrate.

* * * * *